United States Patent [19]

Wykes et al.

[11] 4,359,639
[45] Nov. 16, 1982

[54] METHOD OF AND APPARATUS FOR DETERMINING THE NATURE OF TRANSPORTED MATERIAL

[75] Inventors: John S. Wykes, Derby; Piotr M. Surzyn, Burton-on-Trent; Gerard M. Croke, Burton-on-Trent; Ian Adsley, Burton-on-Trent, all of England

[73] Assignee: Coal Industry (Patents) Limited, London, England

[21] Appl. No.: 109,309

[22] Filed: Jan. 3, 1980

[30] Foreign Application Priority Data

Jan. 12, 1979 [GB] United Kingdom ................. 7901186

[51] Int. Cl.³ .......................... G01N 23/00; G21K 1/00
[52] U.S. Cl. ................................. 250/359.1; 250/255; 378/58
[58] Field of Search ................... 250/358 R, 359, 255, 250/505

[56] References Cited

U.S. PATENT DOCUMENTS

| | | | |
|---|---|---|---|
| 3,246,150 | 4/1966 | Stoddart et al. | 250/328 |
| 4,078,178 | 3/1978 | Lowes | 250/252 |
| 4,090,074 | 5/1978 | Watt et al. | 250/358 R |
| 4,200,792 | 4/1980 | Fanger et al. | 250/359 |

Primary Examiner—Alfred E. Smith
Assistant Examiner—Carolyn E. Fields
Attorney, Agent, or Firm—Stevens, Davis, Miller & Mosher

[57] ABSTRACT

A coal/stone mixture transported on a conveyor is investigated by subjecting it to two radiation beams of differing energies. In a preferred embodiment, the higher energy radiation is collimated into a pencil beam and the lower energy radiation into a fan beam. Detector shielding prevents substantial interference of close-to-surface reactions within the detector deriving from the higher energy beam with detection of the lower energy beam.

2 Claims, 10 Drawing Figures

METHOD OF AND APPARATUS FOR DETERMINING THE NATURE OF TRANSPORTED MATERIAL

This invention relates to a method of and apparatus for determining the nature of transported material.

The nature of transported material can be investigated by subjecting the material to radiation and detecting interactions between the radiation and the material. Improvements in such investigations have been made by subjecting the material to radiation of two dissimilar energies and correlating differing interactions of the radiation at the two energies to investigate the nature of the material.

Unfortunately, a problem with such two energy methods is that they have not tended to provide sufficient accuracy for determining the nature of transported material in some applications wherein relatively larger quantities of material are transported, since inelastic scattering of radiation from a relatively higher energy radiation source can interfere substantially with interactions deriving from a relatively lower energy source.

An object of the present invention is to mitigate the above problem, thus to provide a sufficiently accurate method of and apparatus for determining the nature of transported material.

According to one aspect of the present invention, a method of determining the nature of transported material comprises collimating radiation of at least two energies into beams, subjecting the transported material to the beams, detecting the unscattered radiation at said at least two energies after passage through the transported material and deducing from said detected radiation the nature of the transported material.

The radiation is collimated by positioning shielding around a source thereof. The detector is shielded to prevent any substantial interference of close to surface reactions deriving from a relatively higher of the at least two energies of radiation with detection of a relatively lower energy of the at least two energies of radiation. Alternatively, a source of the relatively higher energy radiation is spaced from the source of the relatively lower energy radiation. The relatively lower energy radiation contains an intensity component deriving from natural background radiation and this component is subtracted according to a preselected calibration.

According to another aspect of the present invention, apparatus for determining the nature of transported material comprises a radiation source arrangement for providing radiation of at least two energies, a detector arrangement for detecting unscattered radiation after passage through the transported material and collimator means for collimating the radiation into beams detectable by the detector arrangement.

Preferably, the collimator means comprises shielding disposable around the source of a relatively higher of the two energies to collimate the radiation into a pencil beam. The detector arrangement comprises shielding disposed at the periphery thereof, which shielding inhibits close to surface reactions of scattered higher energy radiation at the detector.

The apparatus further comprises processor means for processing signals derived by the detector arrangement to determine the nature of the transported material. The processor means preferably subtracts a signal component corresponding to natural radiation intensity from the signals.

Three embodiments of the present invention will now be described by way of example only, with reference to the accompanying drawings in which.

The nature of material may be investigated by bombarding the material with electromagnetic energy in the gamma ray part of the spectrum. Gamma rays can interact with matter in ways including the photoelectric effect and Compton effect. Dependent upon the material gamma rays of different energies can interact in different ways, thus for example, gamma rays at one energy can interact substantially solely according to the Compton effect, whereas gamma rays at a different energy can interact according to both of the photoelectric and Compton effect.

Thus considering a situation where a conveyor belt carries a mixture of coal and stone, gamma rays of different energies will interact in different ways. Thus gamma rays of energy 660 keV from for example a cesium 137 source will be attenuated in passage through the coal/stone mixture to a degree dependent substantially upon the mass of material on the belt. This is because the gamma rays are attenuated substantially due to Compton scattering which is largely independent of the type of material and substantially proportional to the electron density in the gamma ray path.

On the other hand, 60 keV gamma rays from for example an Americium 241 source are attenuated in passage through the coal/stone mixture to a degree to some extent proportional to the average atomic number of the element(s) constituting the mixture on the belt. This is because the gamma rays are attenuated largely by photoelectric interactions which require electrons to be bound strongly to the nucleus upon which the respective gamma ray impinges.

From the foregoing, it will be appreciated that it is possible, in principle, to determine both the mass and the nature of material on a belt, provided that appropriate calibration is made of values of attenuation of gamma rays at the two energies, 60 and 660 keV.

Figure 1:
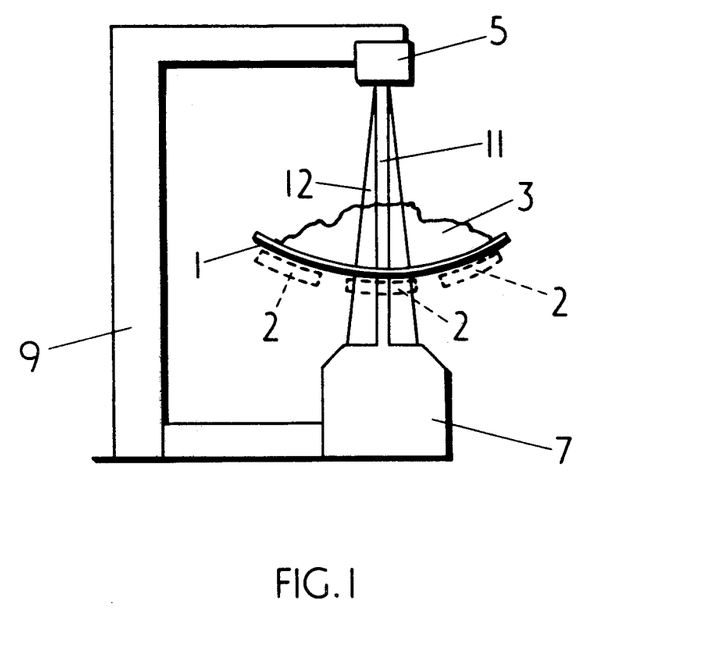
FIG. 1 is an incomplete diagrammatic side view of a first embodiment of the invention including a conveyor installation.

A practical embodiment of apparatus and a method of operation thereof will now be described with reference to FIG. 1. A conveyor is shown at 1 and the conveyor runs upon rollers 2. Sets of rollers are arranged periodically along the belt. A mixture 3 of coal and stone is loaded upon the conveyor 1. A source arrangement 5 of gamma radiation is arranged above the conveyor 1 and a detector 7 for the radiation below the conveyor. The source arrangement 5 and detector 7 are held in a desired juxtaposition by a supportive framework 9.

Two beams of gamma radiation are indicated by 11 and 12 respectively. The beam 11 is a pencil beam and the beam 12 a fan beam. The beam 11 is of a relatively higher energy than the beam 12. The source and detector are situated between the rollers so that the latter do not interfere with the beams.

Figure 2:
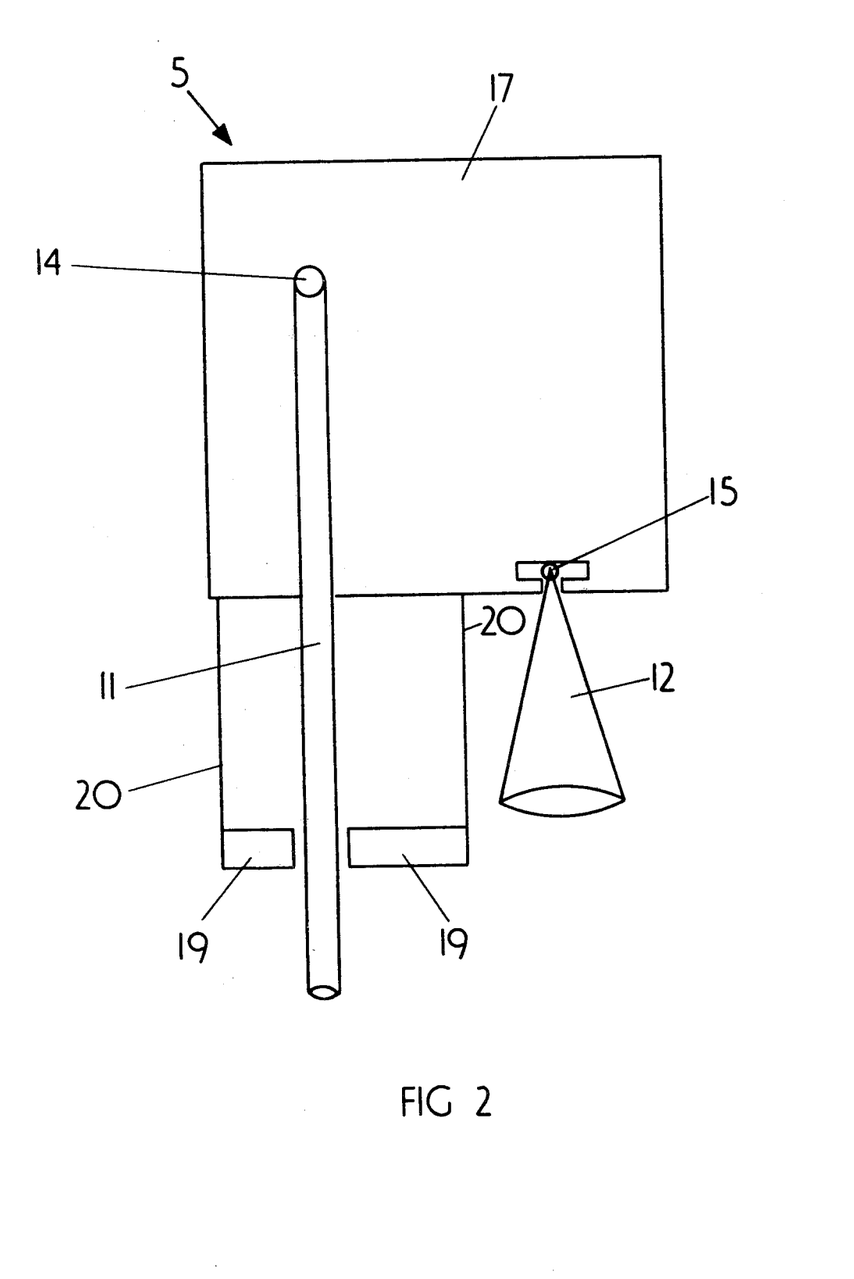
FIG. 2 is a diagrammatic view of part of FIG. 1 showing more detail.

Referring to FIG. 2, the source arrangement 5 of radiation is shown in more detail and the pencil beam 11 can be seen to be derived from a source 14 and the fan beam 12 from a source 15. The source 14 is deeply inset into the source arrangment 5 and the source 15 is not. The source arrangement comprises a holder material 17 which is substantially impermeable to gamma radiation, and which thus causes the pencil and fan beams 11 and 12 respectively to be formed. Further shielding 19 is disposed below the holder material 17 and is retained in position by brackets 20 attached to the holder material 17. The further shielding ensures that a pencil beam of gamma rays is produced and an appropriate use of such shielding may enable the high energy souce not to be deeply inset.

Figure 3:
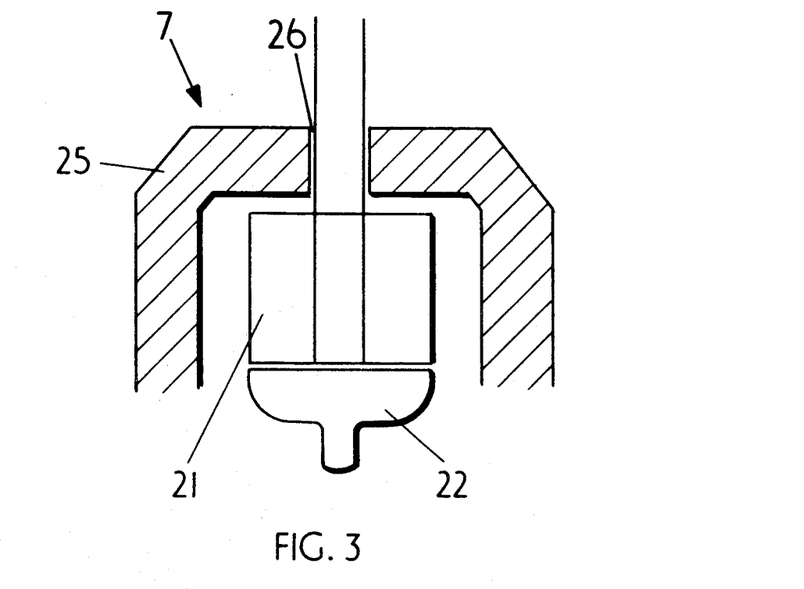
FIG. 3 is a diagrammatic view of another part of FIG. 1 showing more detail.

Referring now to FIG. 3, the detector 7 is shown in more detail. The detector 7 comprises a scintillation crystal 21 and a photomultiplier tube 22. Shielding 25 which is substantially impermeable to gamma radiation is arranged over the crystal and the shielding 25 contains an aperture 26 through which incoming radiation can pass. The scintillation crystal has a generally circular detection area which is of radius of the order of three times as great as the aperture 26. Consequently, the detector has a reduced operational surface area and reactions occurring in the cylinder under the reduced area are surrounded by a crystal annulus and are thus not near the crystal surface. In this way, reactions resulting in escape of most of the gamma energy from the crystal are inhibited because such reactions increase in probability of occurring near the crystal surface.

The lower energy beam can be other than fanned (since inelastic collision resulting therefrom will be of a lower energy and not detected or used by the detector). The higher energy beam is a pencil beam so that inelastic scatterings caused thereby which may interfere with the lower energy channels are reduced. Of course, in operation the same section of the lower energy beam as the higher energy beam will be detected by the detector owing to its shielding.

Figure 4:
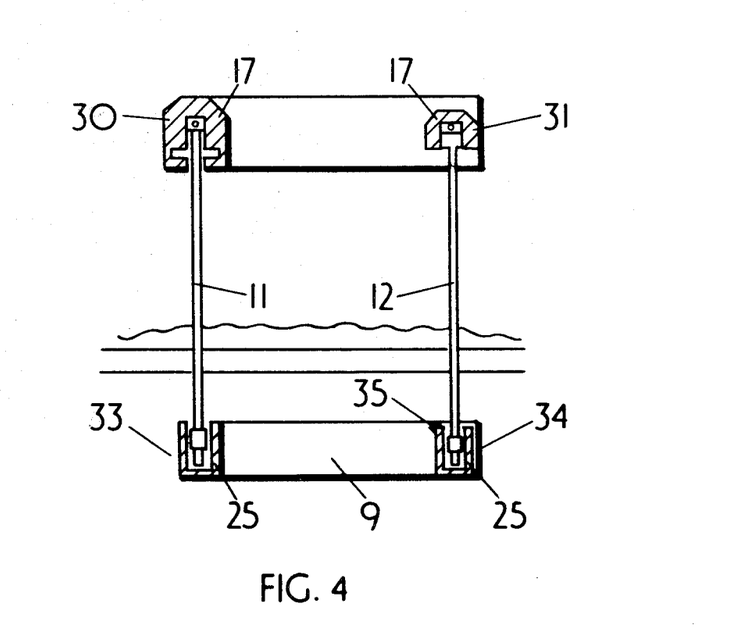
FIG. 4 shows a second embodiment of the invention in a conveyor installation as a diagrammatic elevation.
Figure 5:
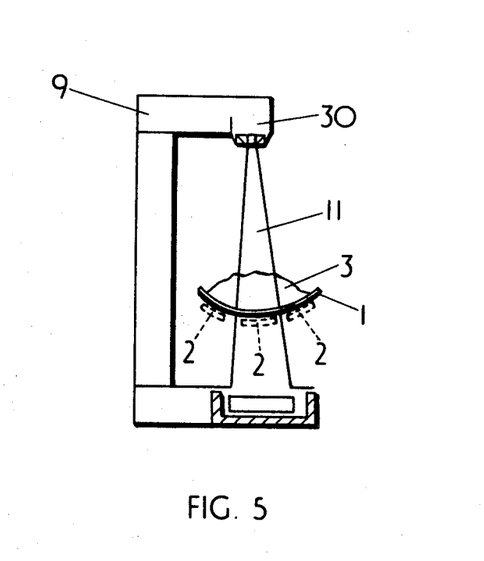
FIG. 5 is a side view of FIG. 4.

Referring to FIG. 4, there is shown a second embodiment of the invention, like reference numerals be used as appropriate. In the second embodiment of the invention, two sources of radiation are shown at 30 and 31 respectively. The source 30 derives a relatively higher energy radiation and the source 31 a relatively lower energy radiation. Detectors 33 and 34 detect the radiation from sources 30 and 31 respectively. The detector 34 is shielded by extra shielding 35 on its side towards the relatively higher energy detector 33. Referring to FIG. 5, it can be seen that the beam of gamma energy from the higher energy source is fanned across the material on the belt.

Figure 6:
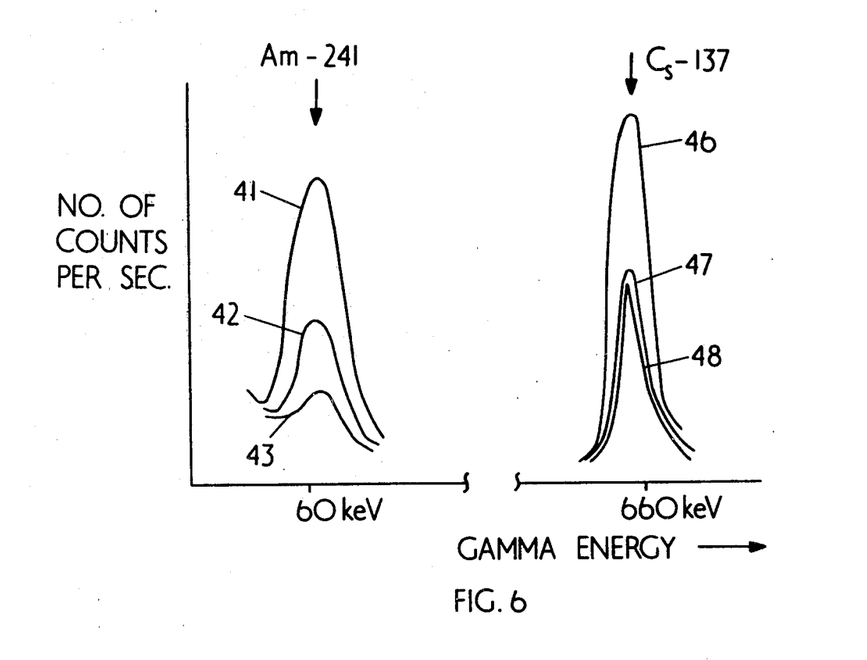
FIG. 6 is a graph showing detected radiation.

Referring to FIG. 6, there is shown a graph with gamma energy plotted as abscissa and number of gamma counts as ordinate. The energy axis is split so that two channels and 60 keV and 660 keV can be shown. A curve 41 shows the count received at 60 keV from the lower energy source when there is no material on the conveyor belt. A curve 42 shows the count received where a density of M kilograms of coal per square meter of belt is on the belt and a curve 43 the count received with the same quantity of stone on the belt. Similar curves are plotted for the higher energy source and these are indicated at 46, 47 and 48. Comparison of the sets of curves 41, 41 and 43 with the set of curves 46, 47 and 48 shows that the same mass of coal or stone (or coal/stone) attenuates radiation from the higher energy source the same amount but the attenuation of the lower energy radiation is dependent upon whether coal or stone is on the belt.

Figure 7:
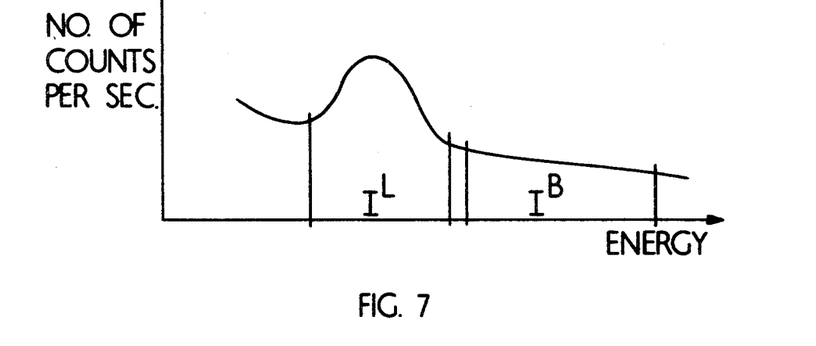
FIG. 7 is a further graph showing detected radiation.

At the lower energy part of the received spectrum, substantial interference can be caused by natural radiation at the energy under investigation. Consequently, it is necessary to quantify this natural radiation so that its effect can be eliminated. Referring to FIG. 7, there is shown a graph with gamma energy as abscissa and received counts per second as ordinate. The gamma energy of the lower energy channel is indicated by a $I^L$. A neighbouring channel which is indicated by $I^B$ and is the correction channel shows counts received at this neighbouring energy owing to natural radiation. Width of the correction channel is chosen so that the intensity $I^B$, i.e. the total number of counts per second in this channel is the same as that occurring in the $I^L$ channel owing to background. In practice, the $I^B$ channel is usually wider in energy than the $I^L$ channel. Consequently, the intensity of radiation owing to the actual low energy source is given by $I = I^L - I^B$.

Figure 8:
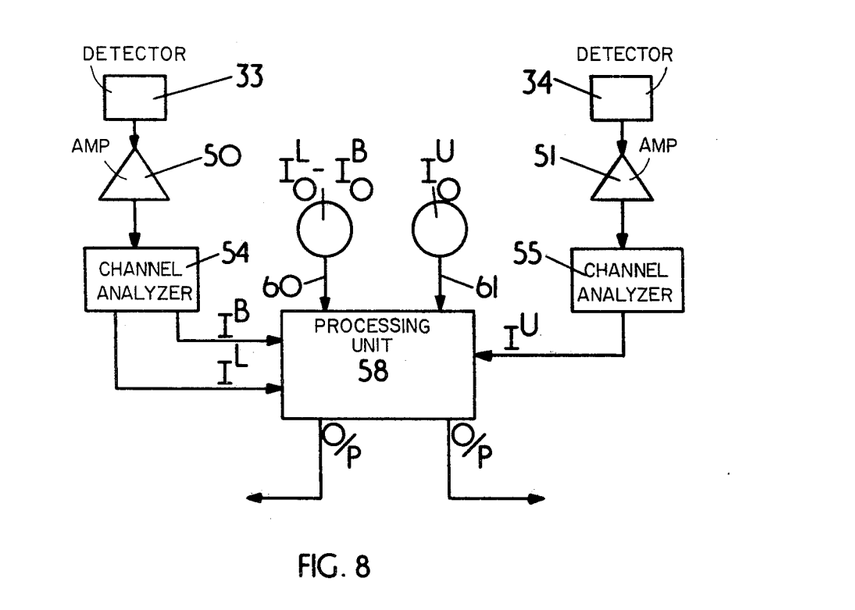
FIG. 8 is a block electrical circuit diagram.

Referring to FIG. 8, electrical circuitry necessary for determining the nature of material on this belt is shown in block form. The detectors 33 and 34 each have associated therewith an amplifier indicated at 50, 51 respectively. The output from the amplifier 50 is fed to a two channel analyser 54, two channels being necessary in order that the background and lower energy level signals can be discriminated according to $I = I^L - I^B$ as mentioned above. The output from the amplifier 51 is fed to a single channel analyser 55. The two channel analyser 54 produces output signals indicative of intensity of background radiation $I^B$ and of the lower energy radiation $I^L$. The single channel analyser produces an output indicative of the intensity of the radiation at the higher energy $I^U$. These output signals $I^B$, $I^L$, and $I^U$ are fed to processing unit 58, which also has calibration inputs 60, 61, which can be provided with signals indicative of empty belt values of the signal $I^B$, $I^L$, and $I^U$, which empty belt signals are indicated by $I_O^B$, $I_O^L$ and $I_O^U$.

Since the value of $I^U$ is $I_O^U$ when there is no material on the belt and the value of $I^U$ tends to zero when a large amount of material is on the belt, the mass of material on the belt M is approximately proportional to $$\ln\left(\frac{I^U}{I_O^U}\right)$$

The mass of material is more accurately expressed according to the following formula:

$$M = F\left\{\ln\left(\frac{I^U}{I_O^U}\right), f\right\},$$

F denoting a simple function incorporating the constant of proportionality in respect of $$\ln\left(\frac{I^U}{I_O^U}\right)$$

and f indicating shale fraction as will be explained below. f can be ignored in this formula without introducing any substantial inaccuracy.

The processing unit 58 performs a calculation according to the above formula to derive an output signal indicative of the mass of material on the belt.

Since, for a given mass of material on the belt the value of $$\ln\left(\frac{I^L - I^B}{I_O^L I_O^B}\right)$$

is proportion to the value of $$\ln\left(\frac{I^U}{I_O^U}\right)$$

when the material is coal alone and divergence away from the value of $$\ln\left(\frac{I^U}{I_O^U}\right)$$

is dependent upon the quantity of shale on the belt, then the fraction of shale or stone on the belt f, mentioned above, is given approximately by $$f = a\left\{\ln\left(\frac{I^U}{I_O^U}\right) \Big/ \ln\left(\frac{I^L - I^B}{I_O^L - I_O^B}\right)\right\}^{-1} \quad \text{Equation 1}$$

where a is a constant of proportionality.

Figure 9:
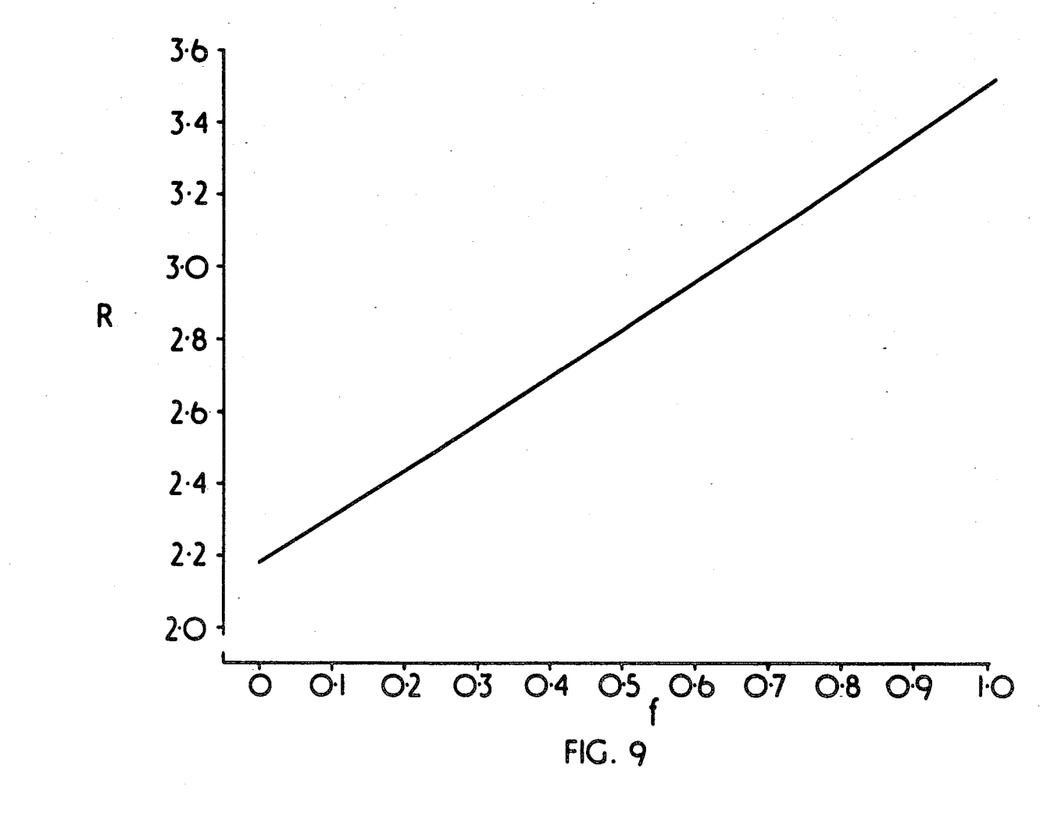
FIG. 9 is a graph showing correlation of parameters.

Referring to FIG. 9, there is shown a graph of R as ordinate versus $f_{actual}$ as abscissa, where $$R = \left\{\ln\left(\frac{I^U}{I_O^U}\right) \Big/ \ln\left(\frac{I^L - I^B}{I_O^L - I_O^B}\right)\right\}^{-1}$$

and $f_{actual}$ is the actual value of the shale fraction on the belt.

A more detailed calculation of shale fraction would give:

$$f = \left[1 - \left(\frac{\rho_C}{\rho_S}\right)\left(\frac{\mu_S^L - R\mu_S^U}{\mu_C^L R\mu_S^L}\right)\right]^{-1} \quad \text{Equation 2}$$

where $\rho_C$, $\rho_S$ are densities of coal and stone, respectively, and $\mu_C$, $\mu_S$ are the linear absorption coefficients of coal and stone respectively indicated by superscripts L, U for the lower and upper energies respectively.

Investigations show that for coal and stone, equation 2 is approximately linear, i.e. f≃kR—b, where k is a constant of proportionality and b is constant.

From the graph it can be seen that the relationship between $f_{actual}$ and R is indeed approximately linear. Consequently, the processing unit 58, which performs a calculation according to the expression $$f = a\left\{\ln\left(\frac{I^U}{I_O^U}\right) \Big/ \ln\left(\frac{I^L - I^B}{I_O^L - I_O^B}\right)\right\}^{-1} b$$

derives an accurate value for the shale fraction of material on the conveyor. The value of f is integrated over time in the processor so that the nature of transported material over a period is determined.

Figure 10:
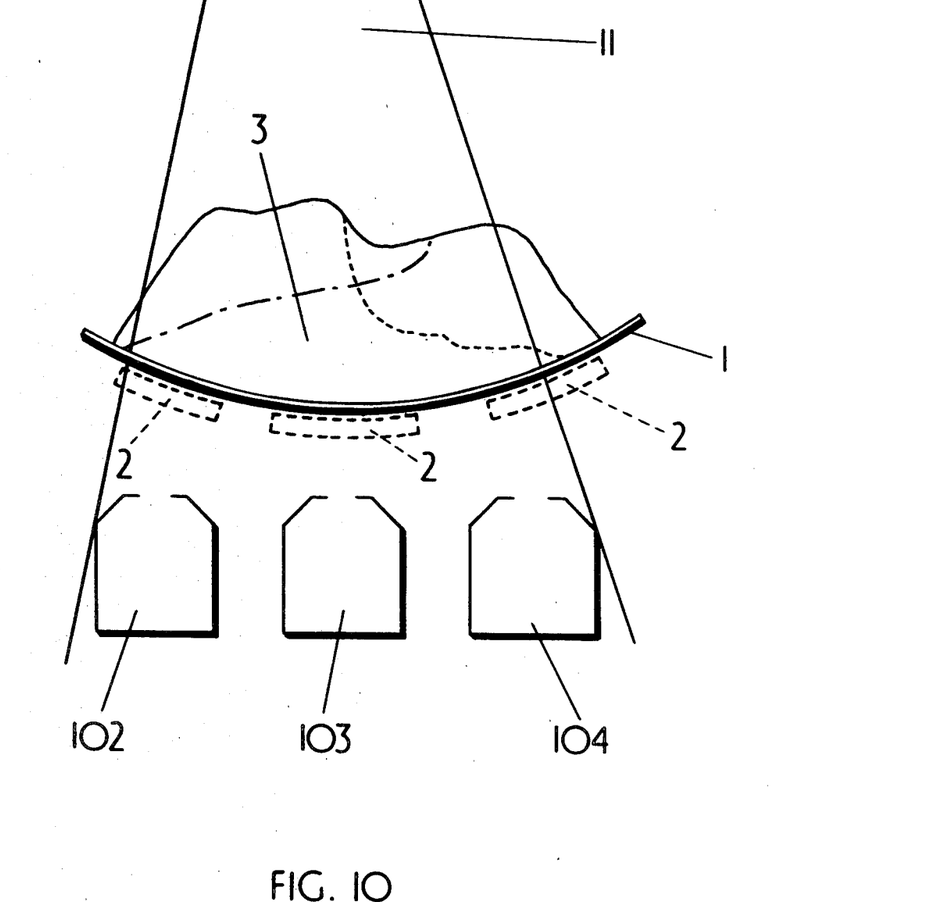
FIG. 10 is a diagrammatic view of a third embodiment of the invention in part of a conveyor installation.

Referring now to FIG. 10, there is shown a third embodiment of the invention, wherein like reference numerals to the first two described embodiments are used as appropriate. From FIG. 10 it can be seen that three detectors 102, 103, 104, are arranged below the conveyor 1. The detectors are all lower energy detectors (although a similar set of three could be provided for higher energy detectors) and all fall within the lower energy radiation fan beam. In a slightly modified form of the third embodiment, a source could be provided for each detector respectively. The advantage of providing three detectors is that three signals of the value of detected valuation can be obtained. Consequently, in situations of uneven belt loading owing to sporadic output from, for example, a number of different coal faces, such situations being indicated in full lines, dotted lines and chain dotted lines in the Figure, the detectors do not indicate that the distribution of material on the belt is substantially uniform, whereas a single detector would.

In operation, the high degree of collimation of the gamma energy beam and scintillation crystal field of view owing to the shielding reduces the effects of downscatter in the load from the higher energy source material on the belt. A crystal larger than the beam diameter is necessary for the above collimation to be used so that at least a 25 mm annulus of scintillation material surrounds the central directly illuminated portion of the crystal. Thus in a typical system employing a two and a half centimeter diameter beam, the beam would impinge upon a crystal of seven and a half centimeters, the outer five centimeter annulus remaining shielded as was explained above. Thus a higher energy gamma ray beam (typically 660 keV energy from a Cs 137 source in these applications) after suffering an inelastic collision in the central portion of the scintillator still has some way to travel before escaping. The probability that it will accomplish this without depositing more than around one tenth of its energy within the crystal (and thereby appearing within the lower energy channel—typically 60 keV from an Am 241 source) is much reduced. By this means, in a CsI (Na) scintillation crystal of the above dimensions, the counts occurring within the lower energy channel, i.e. within the spectral range of the Am-241 photopeak, due to inelastically scattered higher energy gamma photons are only of the order of 2.5% of those appearing in the higher energy channel, i.e. within the Cs-137 photopeak. Larger annular regions or further "stepping down" of the central portion will cause further reductions in this percentage.

The high degree of collimation of the beam reduces the observed downscatter contribution from the material load, i.e. those gamma photons inelastically scattered to this energy before entering the crystal, to the order of one tenth of this value for normal conveyor loads, so that this contribution may be ignored and a constant "down-scatter correction", fixed by the crystal geometry, may be taken. Thus for example, 2.5% of the higher channel counts is subtracted from those in the lower channel to obtain the actual lower channel signal level. Some improvements in the accuracy of this correction may be obtained by allowing for the material downscatter contributions (as opposed to the crystal contribution) to this observed downscatter. Thus in the present case $I^L_{signal} = I^L - 2.5 \times 10^{-2} I^U$ is taken for no material scattering correction and, $$I^L_{signal} = I^L - \left[ 2.5 \times 10^{-2} - 2 \times 10^{-3} \ln\left(\frac{I^U}{I^U_0}\right) \right]$$

is taken to allow some material downscatter correction, the latter term in the parenthesis being proportional to the mass of material on the belt as explained above.

However, for typical conveyor belt loads in mines ($\sim 100$ kg/m$^2$) such downscatter reduction and correction techniques are unlikely to yield compositional accuracies better than $\pm 10\%$ shale fraction since the first and second terms in the above expressions are still of comparable magnitude due to the very low levels of $I^L$ penetrating such loads. Increasing the activity of the lower energy source, and thereby the lower energy signal, is limited by the maximum count-rate handling ability of the counting system. If the maximum count-rate handleable by the system is $I_{max}$ then obviously $I_0^L + I_0^U$ must be less than or equal to $I_{max}$. Within this constraint the relative source strengths of the higher and lower energies should be chosen so as to minimise the resultant error in f, the shale fraction. For typical mine loadings and an $I_{max}$ of 25,000 counts per second an Americium 241 Cesium - 137 system should have relative gamma activities of about two to one.

The requirements of a high degree of collimation to reduce the downscatter contribution from the scattering in the material usually means that only a small segment of the conveyor can be sampled by any one sensor. This means that in a typical mining situation the sampling errors will be large unless a larger number of sensing systems is used (thereby greatly increasing the cost).

In the second embodiment of the invention both higher accuracies can be achieved and larger sampling areas can be employed. The higher and lower energy gamma beams are physically separated and beamed into separate scintillation crystals. The channel selection and counting processes are performed separately so that the higher and lower energy data paths are isolated from each other until $I^U$ and $I^L$ have been evaluated. By this means the lower energy data is obtained solely from a scintillator that is not exposed to the upper energy and therefore no downscatter from the higher energy is seen. Collimation of the beams is most necessary in the direction of detector separation and not in the direction normal to this so that if the two beams are separated along the direction of travel of the conveyor little collimation is necessary across the conveyor and so much wider portions of the belt can be sampled with a single sensor.

The main source of "noise" in the lower energy channel is now the natural background radiation. This may comprise two main parts, that due to the general environment and that due to any active species in the mineral on the belt. Both components will vary with the quantity and composition of the load on the belt, the first due to the change in shielding presented by varying loads to the environmental background and the second because of the change in total activity on the belt. For further improvements in accuracy dynamic corrections must be made for this. Fortunately although the magnitude of the background may vary considerably the background spectrum shape of these energies is relatively stable. Thus the second channel in the lower energy detection apparatus is of such an energy width that the amount of natural background in that segment of spectrum is equal to the amount in the lower energy channel itself. The "background" channel is situated immediately above (in energy) the lower energy channel and the channel width empirically determined so that the above condition holds. The width can be adjusted from site to site. However, it is likely that the width would remain substantially constant in most installations. The data routes for this third system are shown schematically in FIG. 8 as described above. It should also be noted that the count-rate constraint is now $I_0^U$ or $I_0^L$ is less than or equal to $I_{max}$ allowing maximum lower energy source strength. In practice it is not usually necessary to have $I_0^U$ approach $I_{max}$, as the greater shielding problem is not justified by the small increase in accuracy.

From the above description it can be seen that an improved method of and apparatus for determining the nature of transported material is provided.

We claim:

1. A method of determining the nature of transported material, comprising the steps of collimating radiation into two beams by positioning shielding around a source of at least two different energies, a lower of said energies being collimated into a fan beam, and a higher of said energies being collimated into a pencil beam, subjecting the transported material to the beams, detecting with a detector unscattered radiation after passage of the beams through the transported material, and shielding said detector to prevent any substantial interference of close to surface reactions occuring near the detector surface deriving from the relatively higher energy radiation with detection of the lower energy radiation; and analyzing from the detected radiation the nature of the transported material.

2. A method according to claim 1, wherein a source of a relatively higher energy radiation is laterally spaced from a source of a relatively lower energy radiation in an area through which the material is transported.

* * * * *